United States Patent
Satou et al.

(10) Patent No.: US 11,192,854 B2
(45) Date of Patent: Dec. 7, 2021

(54) METHOD FOR PRODUCING SEMICARBAZIDE COMPOUND

(71) Applicants: TOKUYAMA CORPORATION, Yamaguchi (JP); JEOL Ltd., Tokyo (JP)

(72) Inventors: Makoto Satou, Yamaguchi (JP); Misao Matsushige, Yamaguchi (JP); Seketsu Fukuzawa, Tokyo (JP); Masaki Takiwaki, Tokyo (JP)

(73) Assignees: TOKUYAMA CORPORATION, Tokyo (JP); JOEL LTD., Tokyo (JP)

( * ) Notice: Subject to any disclaimer, the term of this patent is extended or adjusted under 35 U.S.C. 154(b) by 0 days.

(21) Appl. No.: 16/957,550

(22) PCT Filed: Jun. 11, 2019

(86) PCT No.: PCT/JP2019/023164
§ 371 (c)(1),
(2) Date: Jun. 24, 2020

(87) PCT Pub. No.: WO2019/240141
PCT Pub. Date: Dec. 19, 2019

(65) Prior Publication Data
US 2021/0002212 A1   Jan. 7, 2021

(30) Foreign Application Priority Data

Jun. 12, 2018 (JP) .............................. JP2018-112193

(51) Int. Cl.
*C07C 281/06* (2006.01)
(52) U.S. Cl.
CPC .................................. *C07C 281/06* (2013.01)
(58) Field of Classification Search
None
See application file for complete search history.

(56) References Cited

U.S. PATENT DOCUMENTS

| 7,019,146 B1 | 3/2006 | Ishigai et al. |
| 2003/0119670 A1* | 6/2003 | Araki .................... C07C 309/66 504/116.1 |
| 2018/0088137 A1 | 3/2018 | Higashi et al. |

FOREIGN PATENT DOCUMENTS

| JP | 2013-518258 A | 5/2013 |
| JP | 2018-054459 A | 4/2018 |
| WO | WO 2002103340 | * 12/2002 |
| WO | 2004-002996 A1 | 1/2004 |
| WO | 2011-091436 A1 | 7/2011 |

OTHER PUBLICATIONS

Rodríguez-Spong et al. Adv. Drug Delivery Rev. 56 (2004) 241-274.*
Ogawa et al. Rapid Commun. Mass Spectrom. 2013, 27, 2453-2460.*
Deindoerfer Journal of Materials Chemistry (2006), 16(4), 351-358.*
G.W. Breton, et al., "Alternative synthetic routes to N-methyl-1,2,4-triazoline-3,5-dione (MeTAD) and other triazolinedione derivatives," Tetrahedron Letters, vol. 55, (2014), pp. 4661-4663.
Chinese Office Action, dated Aug. 11, 2020, corresponding to Chinese Office Action 201980005867.7.
S.Mallakpour, et al., Journal of Applied Polimer Science, 103(2) (2007) 947-954.
S. Ogawa, et al., A novel Cookson-type reagent for enhancing sensitivity and specificity in assessment of infant vitamin D status using liquid chromatography/ tandem mass spectrometry, Rapid Commun. Mass Spectrom., vol. 27, 2013, p. 2453-2460.
G.W. Breton, et al., "Supplementary Content," Tetrahedron Letters, vol. 28, (Jun. 28, 2014), pp. 1-14 XP55836117.

* cited by examiner

*Primary Examiner* — Ana Z Muresan
(74) *Attorney, Agent, or Firm* — Hogan Lovells US LLP

(57) ABSTRACT

Provided is a method for producing a high-purity, high-quality semicarbazide compound at a high yield by a simple method. The semicarbazide compound is recrystallized by a solvent containing a halogenated hydrocarbon. Dichloromethane is preferred as the halogenated hydrocarbon.

3 Claims, No Drawings

METHOD FOR PRODUCING SEMICARBAZIDE COMPOUND

This application is a U.S. National Phase under 35 U.S.C. § 371 of International Application PCT/JP2019/023164, filed on Jun. 11, 2019, which are incorporated herein in their entirety. This application also claims priority to Japanese Patent Application No. 2018-112193, filed on Jun. 12, 2018. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a method of producing a semicarbazide compound. More specifically, the present invention relates to a production method of obtaining a high purity semicarbazide compound by a simple method.

BACKGROUND ART

A compound having a structure of 1,2,4-triazoline-3,5-dione is called a Cookson type reagent and has a property of producing, according to a fast and quantitative Diels-Alder reaction with a diene compound, the corresponding ene compound. For this reason, the compound having a structure of 1,2,4-triazoline-3,5-dione is a compound that is used for synthetic reactions and has high usefulness.

Furthermore, since the compound having a structure of 1,2,4-triazoline-3,5-dione has high reactivity as the Cookson type reagent, use of the compound as a reagent for derivatization of various compounds has been also suggested.

In Non-Patent Document 1, for example, use of 4-dimethylaminophenyl-1,2,4-triazoline-3,5-dione (hereinbelow, abbreviated as "DAPTAD") as a reagent for derivatization of vitamin D3 is described. In Non-Patent Document 1, it is described that a reaction product between DAPTAD and vitamin D3 exhibits higher sensitivity in mass analysis compared to vitamin D3.

As a method of producing such Cookson type reagents, the following synthetic route is disclosed in Non-Patent Document 2.

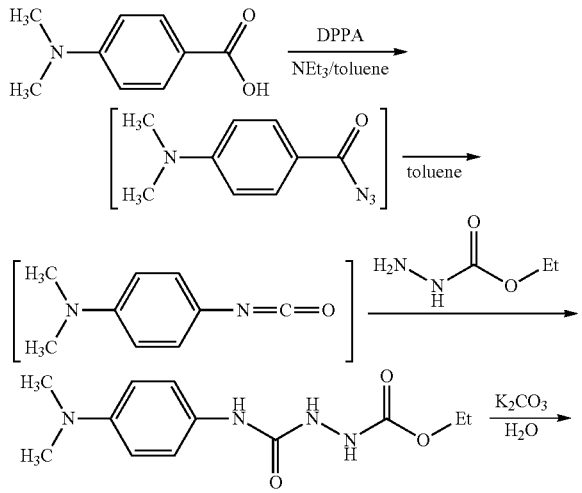

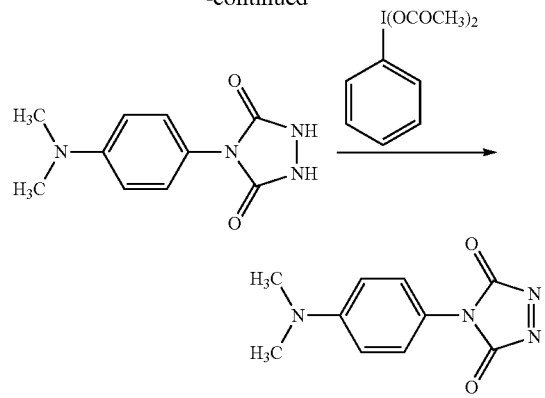

In general, an urazole compound to become a precursor of the Cookson type reagent is synthesized by cyclization of a semicarbazide compound using an alkali reagent. Furthermore, the semicarbazide compound can be produced by reacting an acid azide compound (via isocyanate, en route) with a carbazinic acid ester (see, Patent Documents 1 and 2, and Non-Patent Document 1).

Patent Document 1: Japanese Unexamined Patent Application (Translation of PCT Application), Publication No. 2013-518258

Patent Document 2: PCT International Publication No. WO2004/002996

Non-Patent Document 1: S. Mallakpour, et al., Journal of Applied Polymer Science, 103(2)(2007) 947-954

Non-Patent Document 2: Ogawa, et al., Rapid Commun. Mass Spectrom, 27(2013) 2453-2460

DISCLOSURE OF THE INVENTION

Means for Solving the Problems

The compound having a structure of 1,2,4-triazoline-3,5-dione, which is represented by DAPTAD, exhibits very high reactivity with a diene compound but is a very unstable compound, and a method for purification thereof is not established yet.

In this regard, inventors of the present invention produced a semicarbazide compound according to the method described in Non-Patent Document 1, and carried out an analysis by high performance liquid chromatography (HPLC) for the obtained semicarbazide compound. As a result, it was found that chemical purity (HPLC purity) of the obtained semicarbazide compound is 80 to 90%, and there is a room for improvement in terms of the purity.

Furthermore, it was also found that, when an urazole compound is synthesized by using, as a raw material, a semicarbazide compound containing plural impurities and a Cookson type reagent is further produced from the urazole compound, the purity of the obtained Cookson type reagent is low.

Therefore, to produce a high purity and high quality Cookson type reagent, it is necessary that the urazole compound to be a precursor thereof and also the semicarbazide compound of the previous step have high purity and high quality.

The present invention is devised in consideration of the necessity described above and provides a method of producing a high purity and high quality semicarbazide compound at high yield by a simple method.

Means for Solving the Problems

To solve the problem described above, the inventors of the present invention conducted intensive studies on a method of purifying a semicarbazide compound. As a result, it was found that the impurities contained in the semicarbazide compound are soluble in halogenated hydrocarbons. In addition, it was also found that, when the semicarbazide compound is recrystallized in a solvent containing halogenated hydrocarbons, a high purity and high quality semicarbazide compound can be obtained with good efficiency, and thus the present invention is completed.

Namely, the present invention is a method of producing a semicarbazide compound, the method including a recrystallization step in which a semicarbazide compound represented by the following Formula (1) is recrystallized in a solvent containing halogenated hydrocarbons:

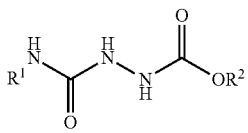
(1)

wherein $R^1$ is an organic group and $R^2$ is a group selected from the group consisting of an alkyl group, an aralkyl group, and a substituted phenyl group which have 1 to 20 carbon atoms and may include an oxygen atom.

The halogenated hydrocarbons may be dichloromethane.

$R^1$ in the above Formula (1) may be a phenyl group which may have a substituent.

A semicarbazide compound represented by the above Formula (1) may be a compound obtained by reacting an acid azide compound represented by the following Formula (2) with a carbazinic acid ester compound represented by the following Formula (3):

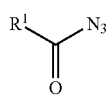
(2)

wherein $R^1$ is the same as the above Formula (1),

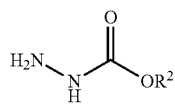
(3)

wherein $R^2$ is the same as the above Formula (1).

Effects of the Invention

According to the method of producing a semicarbazide compound of the present invention, the type and amount of impurities contained in the semicarbazide compound can be reduced, and a semicarbazide compound having high chemical purity and stable product quality can be produced.

PREFERRED MODE FOR CARRYING OUT THE INVENTION

<Method of Producing Semicarbazide Compound>

The present invention is a method of producing a semicarbazide compound, the method including a recrystallization step in which a semicarbazide compound represented by the following Formula (1) is recrystallized in a solvent containing halogenated hydrocarbons. According to the present invention, a semicarbazide compound with high chemical purity can be obtained at high yield.

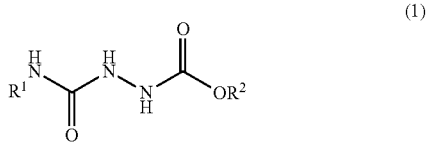
(1)

Wherein $R^1$ is an organic group and $R^2$ is a group selected from the group consisting of an alkyl group, an aralkyl group, and a substituted phenyl group which have 1 to 20 carbon atoms and may include an oxygen atom.

Hereinbelow, a semicarbazide compound represented by the above Formula (1) before carrying out the production method of the present invention is referred to as a "crude semicarbazide compound".

Details of the reason for being capable of obtaining a high purity semicarbazide compound according to the production method of the present invention remain unclear; however, it is presumed by the inventors of the present invention as follows. Namely, impurities contained during the production of a crude semicarbazide compound are presumably impurities that are generated mainly as a by-product during azidation. Since the semicarbazide compound has a poor solubility in halogenated hydrocarbons while the by-products are soluble in the halogenated hydrocarbons, it is presumed that a high purity semicarbazide compound can be obtained by carrying out recrystallization of a semicarbazide compound containing impurities in a solution which contains halogenated hydrocarbons.

[Semicarbazide Compound]

The semicarbazide compound used for the production method of the present invention has a structure represented by the above Formula (1).

Herein, $R^1$ in the above Formula (1) is preferably selected from the group consisting of a phenyl group, a nitrogen-containing heterocyclic group, and an alkyl group which may contain a disubstituted amino group or a disubstituted aminoalkyl group substituted with the same or different alkyl group, aralkyl group, or aryl group which may include an oxygen atom or a nitrogen atom, a nitro group, a ferrocenyl group, or a quinoxalinyl group having a substituent.

More preferably, $R^1$ in the above Formula (1) is a group selected from the group consisting of a phenyl group, a methyl group, and an ethyl group, either substituted or non-substituted.

Particularly preferably, $R^1$ in the above Formula (1) is a group selected from the group consisting of a phenyl group, a methyl group, a 2-(6,7-dimethoxy-4-methyl-3-oxo-3,4-dihydroquinoxalinyl)ethyl group, a 4-nitrophenyl group, a ferrocenylmethyl group, a 4-dimethylaminophenyl group, and a 4-dimethylaminomethylphenyl group. The semicarbazide compound of the above Formula (1) with such groups may be a Cookson type derivatizing agent.

Furthermore, $R^2$ in the above Formula (1) is preferably selected from the group consisting of an alkyl group, an aralkyl group, and a phenyl group having 1 to 8 carbon atoms.

Particularly preferably, from the viewpoint of the easy obtainability, cost, or the like, $R^2$ in the above Formula (1) is an alkyl group having 1 to 4 carbon atoms.

As the semicarbazide compound having a structure represented by the above Formula (1) that is used for the production method of the present invention, 1-ethoxycarbonyl-4-(4'-dimethylaminophenyl)semicarbazide to be a raw material of DAPTAD is particularly preferable.

As the semicarbazide compound having a structure represented by the above Formula (1) that is used for the production method of the present invention, a compound produced by a known method can be used without any particular limitation. In particular, from the viewpoint of having a high effect of removing impurities, it is preferable to use a semicarbazide compound obtained by reacting an acid azide compound represented by the Formula (2) and a carbazinic acid ester compound represented by the Formula (3) that are described below.

[Recrystallization Step]

The method of producing a semicarbazide compound according to the present invention includes a recrystallization step in which a semicarbazide compound is recrystallized in a solvent containing halogenated hydrocarbons.

(Solvent Containing Halogenated Hydrocarbons)

The halogenated hydrocarbons included in a solvent used for the recrystallization step is not particularly limited, and examples thereof may include dichloromethane, chloroform, carbon tetrachloride, trichloroethane, and 1,2-dichloroethane. Only one type of those halogenated hydrocarbons may be used, and two or more types of the halogenated hydrocarbons may be used after mixing. Among them, it is preferable to use dichloromethane or chloroform. Furthermore, from the viewpoint of purity and yield, it is particularly preferable to use dichloromethane.

In addition, as for the solvent to be used for the recrystallization step, halogenated hydrocarbons may be used after being mixed with a solvent commonly used for recrystallization. An alcohol-based solvent, acetone, ethyl acetate, tetrahydrofuran, toluene, a hydrocarbon-based solvent other than the halogenated hydrocarbons, or the like can be mentioned as such a solvent, for example.

The ratio of the halogenated hydrocarbons in a solvent used for the recrystallization step is preferably set in a range of 60 to 100 parts by mass relative to the whole solvent.

In the present invention, the amount of the solvent used for the recrystallization step is not particularly limited. The amount of the solvent may be suitably determined depending on conditions such as the amount of a crude semicarbazide compound, the amount of impurities, the type of a solvent to be used, or temperature.

When dichloromethane is used for the recrystallization step, for example, dichloromethane is preferably used so as to be in a range of 50 to 120 mL relative to 1 gram of the crude semicarbazide compound. In the case of using chloroform, chloroform is preferably used so as to be in a range of 10 to 50 mL relative to 1 gram of the crude semicarbazide compound.

(Conditions for Recrystallization)

In the recrystallization step of the present invention, the temperature at the time of dissolving the crude semicarbazide compound in a solvent may be suitably determined depending on the amount and concentration of the crude semicarbazide compound, the amount of impurities, the type of a solvent, or the like. To obtain a high purity semicarbazide compound at high yield, the temperature is preferably set in a range of 30 to 60° C. Furthermore, when dichloromethane is used, the temperature is preferably set in a range of 30 to 39° C.

As for the method of dissolving the crude semicarbazide compound in a solvent, dissolving is made generally under stirring, although not particularly limited thereto. When insolubles are present as impurities, the insolubles may be subjected to a filtering separation treatment. Furthermore, it is also possible that a large amount of a recrystallization solvent is added and concentration of the solvent is carried out thereafter.

In the recrystallization step of the present invention, the temperature for cooling a solution in which the crude semicarbazide compound is dissolved may be suitably determined depending on the amount of impurities, the concentration of the semicarbazide compound, the type, composition, or the like of a solvent. From the viewpoint of yield and operability, cooling to a range of −20° C. to 10° C. is preferable. In addition, the cooling rate is not particularly limited. The time for maintaining at the cooling temperature is, although not particularly limited, generally about 3 to 40 hours. Furthermore, cooling to the final cooling temperature may be achieved at the first stage, or, after maintaining once at an intermediate temperature, cooling to the final cooling temperature may be achieved.

The method of producing a semicarbazide compound including the recrystallization step of the present invention allows, by single implementation, obtainment of high purity semicarbazide. When dichloromethane is used as halogenated hydrocarbons, in particular, a semicarbazide compound with sufficiently high purity can be obtained only with single implementation. Meanwhile, for the purpose of obtaining semicarbazide with even higher purity, the recrystallization step of the present invention can be repeatedly implemented.

Crystals of the semicarbazide compound precipitated by the method of producing a semicarbazide compound of the present invention can be isolated by solid-liquid separation by filtration, centrifugal separation, or the like followed by drying by natural drying, air blow drying, vacuum drying, or the like.

<Method of Synthesizing Semicarbazide Compound>

As for the semicarbazide compound having a structure represented by the above Formula (1) that is used for the production method of the present invention, from the viewpoint of having a high effect of removing impurities, it is preferable to use a semicarbazide compound obtained by reacting an acid azide compound represented by the following Formula (2) with a carbazinic acid ester compound represented by the following Formula (3).

(2)

Wherein $R^1$ is the same as the above Formula (1).

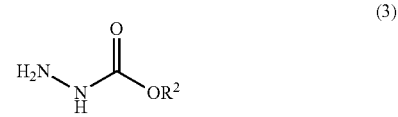

(3)

Wherein R² is the same as the above Formula (1).

[Acid Azide Compound]

As for the acid azide compound represented by the above Formula (2), an industrially obtainable compound can be directly used. In addition, a compound produced by a well known method can also be used. The acid azide compound can be produced, in general, by reacting carboxylic acid or acid chloride with azide for azidation.

Carboxylic acid or acid chloride to be a raw material of the acid azide compound is not particularly limited as long as it is well known. To obtain a semicarbazide compound that can be preferably used for the method of producing a semicarbazide compound of the present invention, it is preferable to use benzoyl chloride, 4-dimethylaminobenzoic acid, 4-dimethylaminobenzoyl chloride, 4-dimethylaminomethylbenzoyl chloride, or the like as the carboxylic acid or acid chloride to be a raw material of an acid azide compound represented by the above Formula (2).

Furthermore, the azide to be a raw material of an acid azide compound is not particularly limited as long as it is well known. Sodium azide, diphenyl phosphoric acid azide, or the like is mentioned, but, from the viewpoint of safety, diphenyl phosphoric acid azide is preferable.

A method of producing an acid azide compound is not particularly limited, and examples thereof include a method of reacting acid chloride with sodium azide in acetone and a method of reacting carboxylic acid with diphenyl phosphoric acid azide in toluene in the presence of triethylamine. From the viewpoint of the easiness and safety of the reaction, the latter is more preferable.

The acid azide compound represented by the above Formula (2) may be used after solidification following isolation, or may be used in a solution state without being isolated from the production process.

[Carbazinic Acid Ester Compound]

As for the carbazinic acid ester compound represented by the above Formula (3), an industrially obtainable compound can be used directly. In addition, a compound produced by a well known method can be also used. The carbazinic acid ester compound can be synthesized, in general, by reacting diethyl carbonate with hydrazine.

The carbazinic acid ester compound represented by the above Formula (3) can be used without any particular limitation as long as it is well known. In particular, from the viewpoint of the easiness of the reaction and obtainability, ethyl carbazinate is preferable.

[Conditions for Reaction]

(Curtius Rearrangement)

After being subjected to Curtius rearrangement in a reaction system, the acid azide compound represented by the above Formula (2) is reacted, as an isocyanate compound, with a carbazinic acid ester compound. Reaction from an acid azide compound to an isocyanate compound is not particularly limited as long as it is well known. In general, Curtius rearrangement is caused with generation of nitrogen by heating.

As a reaction solvent to be used for Curtius rearrangement, a dehydrated solvent is preferable from the viewpoint of the stability of an acid azide compound and an isocyanate compound, and, in particular, it is preferable to use dehydrated toluene. From the viewpoint of the easiness of the progress and control of the reaction, the reaction temperature may be suitably set in a range of 10 to 120° C. The reaction time can be determined by confirming thin layer chromatography (hereinbelow, abbreviated as "TLC") and confirming the loss of the acid azide compound. The reaction time is not particularly limited as long as the loss of the acid azide compound can be confirmed, but 1 hour or longer is sufficient in general.

For example, after reacting 4-dimethylaminobenzoyl azide in toluene for 1 hour at 90° C., by additionally performing reflux for 1 hour at 106° C., 4-dimethylaminobenzoyl isocyanate can be produced.

(Reaction Between Isocyanate Compound and Carbazinic Acid Ester Compound)

After producing the isocyanate compound in a reaction system, the isocyanate compound is subsequently reacted with a carbazinic acid ester compound. If isolation as an isocyanate compound can be made, the isocyanate compound can be isolated and then used for the reaction, but the isocyanate compound can also be directly used for the reaction without any isolation.

The use amount of the carbazinic acid ester compound is not particularly limited, but, from the viewpoint of purification efficiency, the carbazinic acid ester in a range of 0.7 to 1.3 mol relative to 1 mol of the acid azide compound (that is, 1 mol of isocyanate compound) is preferable.

The reaction between the isocyanate compound and carbazinic acid ester compound can be carried out by mixing both of them. For example, both of them are preferably mixed in a reaction solvent by stirring under nitrogen flow.

As for the reaction solvent, a dehydrated solvent is preferable from the viewpoint of the stability of the isocyanate compound, and, in particular, it is preferable to use dehydrated toluene. Furthermore, it is preferable to use a solvent that is common to the reaction for producing an isocyanate compound from the acid azide compound from the viewpoint of operability.

The temperature for reaction between the isocyanate compound and the carbazinic acid ester compound may be suitably set in a range of 10 to 120° C. from the viewpoint of the easiness of the progress and control of the reaction. The reaction time can be determined by confirming TLC and confirming the loss of the isocyanate compound. The reaction time is not particularly limited as long as the loss of the isocyanate compound can be confirmed, but 1 hour or longer is sufficient in general.

Termination of the reaction between the isocyanate compound and carbazinic acid ester compound is carried out by cooling and addition of a solvent or water. The amount of a solvent or water to be added is not particularly limited and can be suitably determined depending on the type of a solvent for addition, the reaction conditions, the operability thereafter, or the like. In general, the amount thereof is preferably at least 5 mL per gram of the semicarbazide compound. The precipitated crude semicarbazide compound can be isolated by solid-liquid separation by filtration, centrifugal separation, or the like followed by drying by natural drying, air blow drying, vacuum drying, or the like.

The crude semicarbazide compound obtained as described in the above is generally a solid with pale yellow to white, although the crude semicarbazide compound is affected by an acid azide compound to be used and the state of the reaction into an isocyanate compound, the purity of a carbazinic acid ester compound, the degree of purification, and a reaction solvent. According to HPLC measurement, the chemical purity (HPLC purity) is generally about 75 to 95%.

EXAMPLES

Hereinbelow, the present invention will be described in more detail by means of Examples, but the present invention is not limited by these Examples.

<Measurement of Chemical Purity (HPLC Purity)>

Measurement of the purity of a semicarbazide compound of the present invention was carried out by using HPLC at the following conditions. The HPLC purity was calculated as an area % of the semicarbazide compound in HPLC measurement.

(Measurement Conditions)
Device: High performance liquid chromatograph (manufactured by Nihon Waters K.K., 2695)
Detector: UV visible spectroscopic detector (manufactured by Nihon Waters K.K., 2489)
Wavelength for detection: 210 nm
Column: Inertsil ODS-3 (5 μm, 4.6×250 mm) (manufactured by GL Sciences Inc.)
Mobile phase A: Phosphate buffer solution (200 mM potassium dihydrogen phosphate, 100 mM sodium 1-pentanesulfonate (ion pairing agent) adjusted to pH=2.0 with hydrochloric acid)
Mobile phase B: Acetonitrile
Liquid transport of mobile phase: Concentration gradient control was made by changing mobile phase A and mobile phase B as shown in Table 1.
Column temperature: Constant temperature near 40° C.
Injection amount: 10 μL
Sample concentration: 0.75 mg/mL

TABLE 1

| Time after injection (Minutes) | Mobile phase A (vol %) | Mobile phase B (vol %) |
|---|---|---|
| 0~10 | 95 | 5 |
| 10~20 | 95→30 | 5→70 |
| 20~30 | 30 | 70 |
| 30~35 | 30→95 | 70→5 |
| 35~40 | 95 | 5 |

Example 1

Synthesis of 4-dimethylaminobenzoyl Azide

To 75 mL of acetone, 1.0 g of 4-dimethylaminobenzoyl chloride was added and cooled on ice. Subsequently, an aqueous solution having 0.50 g of sodium azide dissolved in 2.5 mL of water was added thereto and the reaction was carried out for 1 hour under cooling on ice. After confirming the loss of 4-dimethylaminobenzoyl chloride by TLC, 120 mL of ethyl acetate was added.

The obtained reaction solution was washed 3 times with 120 mL of saturated brine. The organic layer was collected and dried over magnesium sulfate. After separating the magnesium sulfate by filtering, concentration of the organic layer under reduced pressure was carried out to obtain 1.84 g of a solid with pale yellow.

By using hexane/ethyl acetate=4/1 as a developing solvent and Wakosil C-300 (manufactured by FUJIFILM Wako Pure Chemical Corporation) as a filling agent, column purification was performed for the obtained solid with pale yellow. After the column purification, the fraction containing the target product was concentrated under reduced pressure and subsequently subjected to vacuum drying to obtain 0.89 g of 4-dimethylaminobenzoyl azide with pale yellow. The yield was 86.6%.

Synthesis of 1-ethoxycarbonyl-4-(4'-dimethylaminophenyl)semicarbazide

To 50 mL of dehydrated toluene, 0.81 g of 4-dimethylaminobenzoyl azide was added, and stirred for 30 minutes at room temperature (20° C.) under nitrogen flow for dissolving. The temperature of the obtained solution was raised to 90° C., the reaction was allowed to occur for 1 hour, and, additionally, reflux was carried out for 1 hour at 106° C. After confirming the loss of 4-dimethylaminobenzoyl azide by TLC, air cooling to 40° C. was carried out.

When the reaction solution is cooled to 40° C., 0.52 g of ethyl carbazinate was added, and, by stirring for 30 minutes, a white solid was precipitated. Furthermore, after stirring for 1 hour at room temperature (20° C.), the temperature was raised to 106° C. followed by reflux for 1 hour. After that, air cooling to room temperature (20° C.) was carried out so that a solid with pale yellowish white was precipitated.

The precipitated solid was filtered through KIRIYAMA ROHTO and collected to obtain 0.89 g of a crude semicarbazide compound with pale yellow. The chemical purity (HPLC purity) was 92.8%, and the yield was 78.8%.

Recrystallization of 1-ethoxycarbonyl-4-(4'-dimethylaminophenyl)semicarbazide 0.89 g of the obtained crude semicarbazide compound was added to 100 mL of dichloromethane, and the temperature was raised to 35° C. for dissolving the crude semicarbazide compound. Subsequently, the obtained solution was maintained in a temperature range of 0 to 4° C. and stirred for 24 hours.

The precipitated solid was collected by filtering, and then washed with dichloromethane. Subsequently, vacuum drying was carried out at room temperature to obtain 0.81 g of a semicarbazide compound as a white solid. The chemical purity (HPLC purity) was 99.0%, and the yield was 91.0%. The obtained results are shown in Table 2.

TABLE 2

| | Example 1 | Example 2 | Example 3 | Example 4 | Example 5 |
|---|---|---|---|---|---|
| Substituent $R^1$ of crude semicarbazide | 4-Dimethylaminophenyl group | 4-Dimethlylaminophenyl group | 4-Dimethlylaminophenyl group | Phenyl group | Butyl group |
| Chemical (HPLC) purity of crude semicarbazide | 92.8% | 90.3% | 90.3% | 92.3% | 91.8% |
| Recrystallization solvent | Dichoromethane | Dichoromethane | Chloroform | Choroform | Dichoromethane |
| Chemical (HPLC) purity of product purified by recrystallization | 99.0% | 98.8% | 97.0% | 96.2% | 95.0% |
| Recrystallization yield | 91% | 95% | 85% | 90% | 87% |
| Color of product purified by recrystallization | White | White | White | White | White |

Example 2

Synthesis of 4-dimethylaminobenzoyl Azide

To dehydrated toluene, 1.0 g of 4-dimethylaminobenzoic acid was added, and stirring was carried out at room temperature (20° C.) under nitrogen flow. Subsequently, as a result of adding 2.0 g of diphenyl phosphoric acid azide after adding 0.74 g of triethylamine, the temperature has increased up to 40° C. with an occurrence of heat generation. The temperature of the reaction solution was raised to 90° C., and stirring was carried out for 2 hours. The loss of 4-dimethylaminobenzoic acid was confirmed by TLC, and then air cooling to 40° C. was carried out. 4-Dimethylaminobenzoyl azide was directly used, without any isolation, for the synthesis of a crude semicarbazide compound of the next step.

Synthesis of 1-ethoxycarbonyl-4-(4'-dimethylaminophenyl)semicarbazide

To a reaction solution containing the obtained 4-dimethylaminobenzoyl azide, 0.75 g of ethyl carbazinate was added and stirred for 1 hour at room temperature (20° C.). The reaction solution was added with 20 mL of water and stirred additionally for 30 minutes, and the reaction was terminated.

The precipitated solid was collected after filtering through KIRIYAMA ROHTO, and, by washing the collected solid with pale yellow with 5 mL of water, 1.24 g of a crude semicarbazide compound with pale yellow was obtained. The chemical purity (HPLC purity) was 90.3%, and the yield was 77.1%.

Recrystallization of 1-ethoxycarbonyl-4-(4'-dimethylaminophenyl)semicarbazide 1.0 g of the obtained crude semicarbazide compound was added to 110 mL of dichloromethane, and the temperature was raised to 35° C. for dissolving the crude semicarbazide compound. Subsequently, the obtained solution was maintained in a temperature range of 0 to 4° C. and stirred for 24 hours.

The precipitated solid was collected by filtering, and then washed with dichloromethane. Subsequently, vacuum drying was carried out at room temperature to obtain 0.95 g of a semicarbazide compound as a white solid. The chemical purity (HPLC purity) was 98.8%, and the yield was 95.0%. The obtained results are shown in Table 2.

Example 3

Recrystallization of 1-ethoxycarbonyl-4-(4'-dimethylaminophenyl)semicarbazide 1.0 g of the crude semicarbazide compound, which has been synthesized in the same manner as Example 2, was added to 23 mL of chloroform, and the temperature was raised to 60° C. for dissolving the crude semicarbazide compound. Subsequently, the obtained solution was maintained in a temperature range of 0 to 4° C. and stirred for 24 hours.

The precipitated solid was collected by filtering, and then washed with chloroform. Subsequently, vacuum drying was carried out at room temperature to obtain 0.85 g of a semicarbazide compound as a white solid. The chemical purity (HPLC purity) was 97.0%, and the yield was 85%. The obtained results are shown in Table 2.

Example 4

Synthesis of 1-ethoxycarbonyl-4-phenylsemicarbazide

In 10 mL of dehydrated toluene, 1.0 g of ethyl carbazinate was dissolved and cooled on ice. By using a dropping funnel, 1.2 g of phenyl isocyanate (manufactured by Tokyo Chemical Industry Co., Ltd.) was added under nitrogen flow, and, by carrying out stirring for 2 hours at room temperature (20° C.), the reaction was carried out. Furthermore, temperature of the reaction solution was raised to 90° C. and the reaction was allowed to occur for 2 hours, and after that, according to air cooling to room temperature, a solid with pale yellow was precipitated.

The precipitated solid was collected by filtering through KIRIYAMA ROHTO and then washing with toluene to obtain 2.0 g of a crude semicarbazide compound with pale yellow. The chemical purity (HPLC purity) was 92.3%, and the yield was 95%.

Recrystallization of Crude Phenylsemicarbazide 1.0 g of the obtained crude semicarbazide compound was added to 25 mL of chloroform, and the temperature was raised to 60° C. for dissolving the crude semicarbazide compound. Subsequently, the obtained solution was maintained in a temperature range of 0 to 4° C. and stirred for 24 hours.

The precipitated solid was collected by filtering, and then washed with chloroform. Subsequently, vacuum drying was carried out at room temperature to obtain 0.90 g of a semicarbazide compound as a white solid. The chemical purity (HPLC purity) was 96.2%, and the yield was 90%. The obtained results are shown in Table 2.

Example 5

Synthesis of 1-ethoxycarbonyl-4-butylsemicarbazide

In 10 mL of dehydrated toluene, 1.0 g of ethyl carbazinate was dissolved and cooled on ice. By using a dropping funnel, 1.0 g of butyl isocyanate (manufactured by Tokyo Chemical Industry Co., Ltd.) was added under nitrogen flow, and, by carrying out stirring for 2 hours at room temperature (20° C.), the reaction was carried out. Furthermore, the temperature of the reaction solution was raised to 90° C. and the reaction was allowed to occur for 2 hours, and after that, according to air cooling to room temperature, a solid with pale yellow was precipitated.

The precipitated solid was collected by filtering through KIRIYAMA ROHTO and then washing with toluene to obtain 1.87 g of a crude semicarbazide compound with pale yellow. The chemical purity (HPLC purity) was 91.8%, and the yield was 96%.

Recrystallization of Crude Butyl Semicarbazide 1.0 g of the obtained crude semicarbazide compound was added to 100 mL of dichloromethane, and the temperature was raised to 35° C. for dissolving the crude semicarbazide compound. Subsequently, the obtained solution was maintained in a temperature range of 0 to 4° C. and stirred for 24 hours.

The precipitated solid was collected by filtering, and then washed with dichloromethane. Subsequently, vacuum drying was carried out at room temperature to obtain 0.87 g of a semicarbazide compound as a white solid. The chemical purity (HPLC purity) was 95%, and the yield was 87%. The obtained results are shown in Table 2.

Comparative Example 1

Recrystallization of Crude Semicarbazide 1.0 g of the crude semicarbazide compound, which has been synthesized in the same manner as Example 2, was added to 200 mL of toluene, and the temperature was raised to 100° C. for dissolving the crude semicarbazide compound. Subsequently, the obtained solution was maintained in a temperature range of 0 to 4° C. and stirred for 24 hours.

The precipitated solid was collected by filtering, and then washed with toluene. Subsequently, vacuum drying was carried out at room temperature to obtain 0.84 g of a semicarbazide compound as a pale yellow solid. The chemical purity (HPLC purity) was 92.2%, and the yield was 84%. The obtained results are shown in Table 3.

TABLE 3

| | Comparative Example 1 | Comparative Example 2 |
|---|---|---|
| Substituent $R^1$ of crude semicarbazide | 4-Dimethyl-aminophenyl group | 4-Dimethlyl-aminopenyl group |
| Chemical (HPLC) purity of crude semicarbazide | 90.3% | 90.3% |
| Recrystallization solvent | Toluene | Ethyl acetate |
| Chemical (HPLC) purity of product purified by recrystallization | 92.2% | 91.5% |
| Recrystallization yield | 84% | 80% |
| Color of product purified by recrystallization. | Pale yellow | Pale yellow |

Comparative Example 1

Recrystallization of Crude Semicarbazide 1.0 g of the crude semicarbazide compound, which has been synthesized in the same manner as Example 2, was added to 160 mL of ethyl acetate, and the temperature was raised to 75° C. for dissolving the crude semicarbazide compound. Subsequently, the obtained solution was maintained in a temperature range of 0 to 4° C. and stirred for 24 hours.

The precipitated solid was collected by filtering, and then washed with ethyl acetate. Subsequently, vacuum drying was carried out at room temperature to obtain 0.80 g of a semicarbazide compound as a pale yellow solid. The chemical purity (HPLC purity) was 91.5%, and the yield was 80%. The obtained results are shown in Table 3.

The invention claimed is:

1. A method of producing a semicarbazide compound, the method comprising a recrystallization step in which a semicarbazide compound represented by Formula (1) is recrystallized in a solvent containing halogenated hydrocarbons, wherein the halogenated hydrocarbons are dichloromethane:

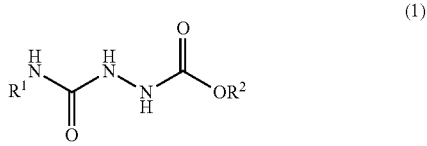

(1)

wherein $R^1$ is a group selected from the group consisting of a phenyl group, a methyl group, a 2-(6,7-dimethoxy-4-methyl-3-oxo-3,4-dihydroquinoxalinyl)ethyl group, a 4-nitrophenyl group, a ferrocenylmethyl group, a 4-dimethylaminophenyl group, and a 4-dimethylaminomethylphenyl group, and $R^2$ is an alkyl group which has 1 to 4 carbon atoms.

2. The method of producing a semicarbazide compound according to claim 1, wherein $R^1$ in Formula (1) is a group selected from the group consisting of a phenyl group, a 4-nitrophenyl group, a 4-dimethylaminophenyl group, and a 4-dimethylaminomethylphenyl group.

3. The method of producing a semicarbazide compound according to claim 1, wherein the semicarbazide compound represented by Formula (1) is obtained by reacting an acid azide compound represented by Formula (2) with a carbazinic acid ester compound represented by Formula (3):

(2)

wherein $R^1$ is the same as in Formula (1),

(3)

wherein $R^2$ is the same as in Formula (1).

* * * * *